US008414857B2

(12) United States Patent
Godber et al.

(10) Patent No.: US 8,414,857 B2
(45) Date of Patent: *Apr. 9, 2013

(54) CALCIUM PHOSPHATE GRANULES OF THE HYDROXYAPATITE TYPE, THEIR PREPARATION PROCESS AND THEIR APPLICATIONS

(75) Inventors: John Godber, Lawrenceville, NJ (US); Lorraine Leite, Brussels (BE)

(73) Assignee: Innophos, Inc., Cranbury, NJ (US)

( * ) Notice: Subject to any disclaimer, the term of this patent is extended or adjusted under 35 U.S.C. 154(b) by 44 days.

This patent is subject to a terminal disclaimer.

(21) Appl. No.: 12/636,028

(22) Filed: Dec. 11, 2009

(65) Prior Publication Data
US 2010/0150806 A1 Jun. 17, 2010

Related U.S. Application Data

(62) Division of application No. 10/564,905, filed as application No. PCT/FR2004/001790 on Aug. 16, 2004, now abandoned.

(51) Int. Cl.
*C01B 15/16* (2006.01)
(52) U.S. Cl. ......... 423/308; 423/465; 502/305; 264/118

(58) Field of Classification Search .................. 423/265, 423/299, 305, 308, 311, 465; 502/305; 514/780; 264/118
See application file for complete search history.

(56) References Cited

PUBLICATIONS

Monma, H.; Kamiya, T.; "Preparation of Hydroxyapatite by the Hydrolysis of Brushite". J. Mater Sci. Dec. 1987. vol. 22 (12). 4248=4250. (Provided by applicant in parent application so not being re-provided).*

* cited by examiner

*Primary Examiner* — Daniel C. McCracken
*Assistant Examiner* — Richard M Rump
(74) *Attorney, Agent, or Firm* — Joanne P. Will

(57) ABSTRACT

The invention concerns calcium phosphates in granular form having an x-ray diffraction pattern characteristic of hydroxyapatite and good compressibility and flow properties in direct compression applications. The invention also concerns the method for preparing said granules characterized in that it comprises processing a suspension of brushite dicalcium phosphate having a certain particle-size distribution using a basic solution, and maintaining the pH at not less than 7.0 for a sufficient time interval to enable the transformation of the brushite calcium phosphate into hydroxyapatite calcium phosphate.

12 Claims, 6 Drawing Sheets

CALCIUM PHOSPHATE GRANULES OF THE HYDROXYAPATITE TYPE, THEIR PREPARATION PROCESS AND THEIR APPLICATIONS

This is a divisional application claiming priority to U.S. patent application Ser. No. 10/564,905 now abandoned, which claims priority to International Application No. PCT/FR04/01790 filed on Aug. 16, 2004, which claims priority to French Application No. 03/08660 filed on Jul. 16, 2003, the contents of each of which is hereby incorporated by reference.

The invention relates to a calcium phosphate excipient and concerns in particular calcium phosphates that have x-ray diffraction patterns characteristic of mineral hydroxyapatite.

More precisely, the invention pertains in particular to calcium phosphates in the form of granules presenting an x-ray diffraction pattern characteristic of hydroxyapatite and good compressibility and flow characteristics in direct compression applications.

The invention also concerns a particularly economical preparation process for said granules.

Finally, the invention also relates to the use of said granules as excipients in the tablets obtained, preferably by direct compression.

The forming of dry materials into tablets is done preferentially by making use of the direct compression technique.

In fact, the direct compression technique requires the fewest treatment steps and the prevents active ingredients from coming into contact with potentially harmful solvents such as water or organic solvents.

The reduction in the number of treatment steps and the absence of solvents reduces costs and thus reduces the degradation of active ingredients.

The formation of tablets by direct compression requires the use of a material in the form of tablets or of a vehicle known under the term excipient. The ideal excipient is one that is nonreactive with regard to the active ingredients in the formulation.

The ideal excipient must also be easily compressible, while forming solid tablets with smooth tablet surfaces. The resistance of the tablet in the majority of applications must also be as high as possible for a minimal compressive force.

The ideal excipient must also flow very well, without any segregation. This is necessary in order to fill the molds of high-speed tableting machines without risk of obstruction and without any variation in the weight of the material that fills the molds.

The majority of powdered materials are impractical for forming tablets by direct compression in high-speed tableting machines due to problems relating to flow.

These powdered materials can often be granulated by various means, for example, by pressure agglomeration, precompression of the powder into granules or by passing the powder between two compression rollers.

Other granulation methods for powders are wet agglomeration followed by drying such as, for example, a rotating-plate agglomeration device or a device in the form of a fluidized bed.

Spray drying, with or without agglomeration additive (for example PVP) can also easily be used.

Precompacting powders to produce materials that flow well often has a harmful effect on the compressibility of the material in granulate form.

These additional steps in treating the excipient add an additional cost and thus make the process less economical.

Using calcium phosphates as excipients is known.

Thus calcium phosphates such as calcium hydrogen phosphate dihydrate [dicalcium phosphate duo-hydrate; $CaHPO_4\cdot 2H_2O$; brushite] anhydrous calcium hydrogen phosphate [anhydrous dicalcium phosphate, $CaHPO_4$; monetite] and hydroxyapatite [$Ca_5(PO_4)_3(OH)$, which is referenced commercially by the term "tricalcium phosphate"].

The ideal chemical formula of hydroxyapatite is $Ca_5(PO_4)_3(OH)$. It is, however, well known in the literature that the crystalline lattice that has this ideal formula is extremely tolerant with regard to substitutions of anions and cations in the lattice.

The substitution of cations with elements such as magnesium, strontium, barium, sodium, lead and a large number of other atoms is well known.

The substitution of anions can take three different forms.

First, a portion of the trivalent phosphate groups ($PO_4^{3-}$) can be replaced by $HPO_4^{2-}$, which leads to a non-stoichiometric apatite.

Second, the trivalent phosphate groups ($PO_4^{3-}$) can be replaced by other complex anions such as carbonates or vanadates.

Third, the hydroxyl group ($OH^-$) can be partially or completely replaced by other anions such as fluoride or chloride.

A coupled substitution in which one ion is replaced by another ion of a different charge and the charge neutrality is maintained by further substitutions in the ions of the lattice with different charges or by vacancies is also well known.

In all these substitutions, the factor that remains common and distinguishes the material as being a hydroxyapatite is its characteristic x-ray diffraction pattern.

Within the scope of the present invention, the term "hydroxyapatite" substantially refers to calcium phosphates that have the x-ray diffraction pattern of hydroxyapatite.

Without tying the scope of the patent to a formula, the phosphates of the invention can be represented by the following formula:

$$Ca_{5-x}(PO4)_{3-x}(HPO_4)_x(OH)_{1-x} \qquad (I)$$

in said formula, x varies between 0 and 1, preferably between 0.1 and 0.5.

The invention includes the case where small quantities, for example, less than 5% by weight and preferably between 0.01 and 3% by weight of calcium, are replaced by another cation, in particular the cation of the base (sodium, potassium).

The invention also includes the case where small quantities of trivalent phosphate groups ($PO_4^{3-}$) are substituted with complex anions (example, carbonate and vanadate), and the hydroxyl ions are replaced by another anion, for example a halide, notably chloride or fluoride.

Calcium phosphates are completely suitable as excipients in a large number of excipient applications due to their intrinsic properties.

They are white. They are stable during storage and do not change from a chemical standpoint in the short term. They are generally stable with regard to the active ingredients and other materials present in a tablet.

Calcium phosphates are generally inert with respect to active ingredients due to their very low solubility in all solvents, especially in water.

They have excellent disintegration profiles with traditional disintegration agents (croscarmellose sodium) and they are compatible with a wide range of active ingredients.

There are a large number of synthesis methods that supply hydroxyapatite as a final product.

They are well known in the literature.

In general, there are two low-temperature methods for preparing hydroxyapatite calcium phosphates, i.e., direct precipitation and hydrolysis.

In the direct precipitation method, sources of calcium and phosphates selected in an appropriate manner react together in water to produce a hydroxyapatite calcium phosphate.

The choice of calcium sources is large, for example calcium hydroxide, calcium chloride, calcium acetate, and calcium nitrate are some of the well-known materials used in direct precipitation of hydroxyapatite calcium phosphate. Calcium hydroxide is preferred.

Sources of phosphate include phosphoric acid, sodium phosphates, ammonium phosphates and potassium phosphates, among others. Phosphoric acid is preferred.

In general, for the direct precipitation method, the initial materials must quite simply a certain water solubility.

Hydroxyapatite calcium phosphate is obtained by precipitation in water of the calcium source and the phosphate source.

The hydrolysis method is based on the fact that hydroxyapatite calcium phosphate is the most stable phase from a thermodynamic standpoint for calcium phosphates in the presence of water.

The hydrolysis of calcium phosphate of the brushite type in aqueous solutions produces hydroxyapatite calcium phosphate.

An example of this method is described according to U.S. Pat. No. 4,335,086 in which the preparation of hydroxyapatite calcium phosphate is described in view of its use in column chromatography.

It is also possible to use brushite and monetite as excipients.

Brushite and monetite of dicalcium phosphates can be synthesized in a direct manner in the form of relatively large particles that have good flow properties.

These materials also have good compressibility characteristics in direct compression applications.

Calcium phosphates are produced most economically by reaction of solutions of phosphoric acid with solutions or suspensions of calcium hydroxide.

Consequently, monetite or brushite can be prepared by varying the relative quantities of calcium and phosphate according to the reaction stoichiometry.

By controlling the addition rates and the concentrations of the reagents, large particles of monetites and brushite can be prepared.

These large particles have good flow and provide high compressibility.

U.S. Pat. No. 5,486,365 teaches a granulation process for brushite calcium phosphate ($CaHPO_4$-$2H_2O$) by spray drying an aqueous suspension of brushite.

Brushite calcium phosphate is crystallized under special conditions requiring the use of organic acids to control the morphology of the brushite crystals.

While dicalcium phosphate brushite and monetite are useful in a large number of applications, they have several disadvantages.

Brushite ($CaHPO_4$-$2H_2O$) contains water making up part of its crystalline structure, which can be released with negative effects, either during tablet preparation or during storage if the material is stored under heat and high humidity conditions (temperatures greater than 40° C.).

This potential release of water can have a negative effect on the active ingredients in the tablet.

Monetite ($CaHPO_4$) does not contain water, but effectively has a low acidity that can also be harmful to certain active ingredients.

These problems are exacerbated in wet method granulation processes due to the necessity of eliminating the solvent, which exaggerates either the release of water for brushite excipients, or the acidity of monetite excipients.

For these reasons, the use of a hydroxyapatite calcium phosphate is envisioned to eliminate both the problem of water and of acid reactions with the active ingredients.

However, unlike brushite and monetite calcium phosphates, it is not possible to produce large particles of hydroxyapatite calcium phosphates having good flow properties directly from calcium hydroxide and phosphoric acid.

Hydroxyapatite, as it is synthesized from phosphoric acid and calcium hydroxide, is well known in the prior art as being a material that does not provide good excipients.

This is linked to two problems, the first of which is the difficulty of directly and economically obtaining large particles of hydroxyapatite.

This is taken into account by the addition of supplemental costly treatment steps such as roller granulation or spray drying.

The second problem has to do with the fact that once large particles are obtained, the product, while being compressible, requires very high compacting forces to produce tablets that are not easily pulverized.

While the causes of this are not understood, and not wishing to be associated with any particular theory, it is believed that these problems are linked to the method used to produce hydroxyapatite.

Consequently, hydroxyapatite is costly to produce in the form of granules that have good flow, and the material that is produced does not have good compressibility characteristics.

In order to overcome the compressibility problems of hydroxyapatite, the preparation of intimate mixtures of hydroxyapatite (which is referred to by the term tricalcium phosphate in the state of the art) with other materials has been proposed.

Thus U.S. Pat. No. 3,987,204 teaches that hydroxyapatite alone is not a useful excipient, but by adding substantial quantities of carob flour to the hydroxyapatite calcium phosphate, a directly compressible material can be produced.

This process involves the use of other constituents and a costly and prolonged mixing treatment, and then drying of the hydroxyapatite/carob flour product.

The addition of microcrystalline cellulose to the hydroxyapatite in order to improve the compressibility characteristics is described in U.S. Pat. No. 4,781,925. The object of this patent is to incorporate disintegration agents into hydroxyapatite tablets for use as a calcium supplement.

Microcrystalline cellulose is well known to provide excellent compressibility characteristics, but it is expensive and its use requires an additional mixing step in the process.

Consequently, it is desirable to have a hydroxyapatite calcium phosphate for reasons of compatibility of the excipient with the active ingredients, while at the same time having a hydroxyapatite that has good flow and compressibility characteristics and that is accessible due to a modest cost.

This type of material has never been available in the state of the art.

One objective of the present invention is to provide an excipient that is useful in a broad range of applications, and that can be used in direct compression or wet granulation processes for tablet production.

Another objective of the present invention is to provide an excipient that is useful in direct compression processes and that has improved compressibility.

An additional objective of the invention is to provide an improved calcium phosphate excipient suitable for direct compression.

An additional objective is to provide a calcium phosphate excipient with free flow properties that has superior compressibility characteristics and that is suitable for direct compression applications.

Another objective of the present invention is to provide an excipient that is economical in terms of production costs.

A first objective of the invention resides in a hydroxyapatite calcium phosphate in granular form.

The granules obtained according to the invention have the physicochemical characteristics specified below.

The definitions and the methods for determining the characteristics given below are specified in the examples.

The granules are white in color.

Thus, the size of the particles can range between 1 and 500 μm.

More precisely, at least 90% by weight of the particles are larger than 10 microns and 90% by weight of the particles are smaller than 300 microns and preferably smaller than 260 microns.

Let us specify that the sizes are determined by sieving on metal sieves.

Generally, the size of the particles expressed by the median diameter ($d_{50}$) is between 100 μm and 250 μm and preferably between 150 μm and 190 μm. The median diameter is defined as being such that 50% by weight of the particles have a diameter larger or smaller than the median diameter.

FIG. 1 represents a photograph taken with a scanning electron microscope that illustrates the morphology of the hydroxyapatite calcium phosphate granules obtained according to the invention.

The hydroxyapatite calcium phosphate granules have a variable density. The apparent density (noncompressed) of the granules is preferably at least 0.6 and is still more preferentially situated between 0.6 and 1.0, preferably between 0.68 and 0.72.

The apparent density (compressed) of the granules is preferably at least 0.7 and is still more preferentially situated between 0.7 and 1.1, preferably between 0.76 and 0.82.

They advantageously have a BET specific surface of between 10 and 100 $m^2/g$, and preferably between 50 and 80 $m^2/g$.

The calcium phosphate granules according to the invention have a cohesion suitable for good flow properties.

The flow index measured at any moment is always much greater than 10.

Hydroxyapatite calcium phosphate granules have superior compressibility characteristics compared to other calcium phosphates.

Thus, the compressibility profile can be defined as follows:
from 15 to 40 KPa for a compression of 30 KN,
from 10 to 25 KPa for a compression of 20 KN,
from 3 to 10 KPa for a compression of 10 KN, The invention therefore resides in calcium phosphate granules having a physical form allowing them to resist attrition, that retain a high internal porosity and, as a result, a rapid rate of dissolution during their use.

It should be noted that the granules have a rapid dissolution rate during their use.

Let us specify that the disintegration rate in water of the granules of the invention is less than 60 seconds, preferably less than 25 seconds and still more preferentially between 5 and 20 seconds. The values given correspond to those obtained by performing the USP 26 (2040) test "Disintegration and dissolution of nutritional supplements" of the American Pharmacopoeia.

The original structure of the products of the invention is obtained by means of a perfectly suited manufacturing process.

Another objective of the invention is the preparation process for said hydroxyapatite calcium phosphate in the form of granules having good flow and compressibility characteristics, characterized by the fact that it comprises treating a brushite dicalcium phosphate suspension having a particle size such that 90% by weight of the particles are smaller than 300 microns, preferably smaller than 260 microns, and 90% by weight of the particles are larger than 10 microns, using a basic solution and keeping the pH at least at 7.0 for a sufficient period of time to permit the transformation of brushite calcium phosphate into hydroxyapatite calcium phosphate.

Preferably, hydrolysis is carried out by heating an aqueous suspension to a temperature and for a period of time sufficient to maintain the pH at a stable level.

According to a first embodiment, which is preferred, the aqueous suspension is heated to the chosen reaction temperature [and] then the base is introduced while regulating the pH.

According to another variant, first the base is added to regulate the pH [and] then the medium is heated to the chosen reaction temperature.

The invention can be better understood by reference to the following general equation for alkaline hydrolysis of brushite into hydroxyapatite:

$$5CaHPO_4 \cdot 2H_2O + 4MOH + H_2O \rightarrow Ca_5(PO_4)_3(OH) + 2M_2HPO_4 + 14H_2O \quad \text{Equation [1]}$$

in which M is the cation provided by the base, preferably an alkali cation, for example $Na^+$, $K^+$, $NH_4^+$. The pH is maintained at a value of at least 7.0 and preferably between 7 and 10 and more preferentially between 8 and 8.5.

The present invention is an improvement in compared to the prior art in that hydroxyapatite calcium phosphate having good flow and compressibility characteristics is directly obtained through the process described above.

The new granular form of hydroxyapatite calcium phosphate leads to numerous advantages when said granules are used as excipients. Thus, they have greater compactibility by direct compression, which, in its turn, provides harder, less friable tablets and reduces the use of binders, and thus reduces costs, reduces the size of the tablets, and reduces the energy required to obtain a desired tablet hardness. Moreover, they allow the use of active ingredients that are not very compatible with brushite and monetite. Due to the granules' improved flow, they lead to better uniformity of composition of the tablets obtained, permitting faster compression rates and permitting the use of drugs or active ingredients with mediocre flow properties.

While it is well known (according to U.S. Pat. No. 4,335,086) that hydroxyapatite can be prepared by means of hydrolysis of calcium hydrogen phosphates, we observed, quite unexpectedly, that due to a selection of the particle size of the initial brushite calcium phosphate, the hydroxyapatite thus formed by alkaline hydrolysis possesses superior compression characteristics both compared to the initial brushite calcium phosphate and to other hydroxyapatite materials produced by different processes.

This new hydroxyapatite calcium phosphate can be prepared by starting with a brushite calcium phosphate prepared by any known process that prepares brushite calcium phosphate as defined here.

In order to obtain a hydroxyapatite calcium phosphate that has good flow characteristics, it must, according to the invention, have a particle-size distribution such that 90% by weight of the particles are smaller than approximately 300 microns, and preferably smaller than approximately 260 microns, and at least 90% by weight of the particles are larger than approximately 10 microns.

In order to do this, the initial brushite calcium phosphate material has a particle-size distribution such that 90% by weight of the particles are smaller than approximately 300 microns, and preferably smaller than 260 microns, and at least 90% by weight of the particles are larger than approximately 10 microns.

This particle-size distribution can be obtained by eliminating particles outside of this range.

The particle-size selection operation is conducted by sieving.

In a preferred embodiment, the size of the particles expressed by the median diameter ($d_{50}$) is between 100 μm and 250 μm and preferably between 150 μm and 190 μm.

Furthermore, since the final hydroxyapatite product must conform to the regulations governing the use of pharmaceutical constituents, the brushite calcium phosphate must also respect the purity requirements relative to pharmaceutical constituents as specified in the Pharmacopoeia.

Thus, the European pharmaceutical specifications for brushite calcium phosphate in the case of use in the pharmaceutical field are such that the content of $CaHPO_4, 2H_2O$ is between 98.0 and 105.5% and the content of chloride ions is less than or equal to 330 ppm; the content of fluoride ions is less than or equal to 100 ppm; the content of arsenic is less than or equal to 10 ppm; heavy metal and iron contents are less than or equal to 40 ppm and 400 ppm, respectively.

In accordance with the process of the invention, a base is used to carry out the hydrolysis reaction; this base may be chosen from among those that are easily soluble in water and that are compatible in view of a use with pharmaceutical constituents in the sense that they do not introduce any undesired material that could contaminate the final product and that could make it inappropriate for use with respect to the requirements of the Pharmacopoeia.

The use of NaOH, $NH_4OH$, $Ca(OH)_2$ and KOH bases is appropriate for the hydrolysis reaction.

Advantageously, a basic aqueous solution having a concentration between 20 and 40% is used.

In the reaction of brushite calcium phosphate with an aqueous alkaline solution, it is preferable to keep the pH in the range of 7.0 to 10.0 and more preferably in the range of 8.0 to 8.5 during the hydrolysis reaction.

It is possible to carry out the hydrolysis at pH values lower than 8.0, but the reaction progresses more rapidly within the above-mentioned range.

Keeping the pH at 7 requires a longer hydrolysis time, but hydrolysis continues nevertheless continue.

Without the addition of a base, the only product produced from brushite calcium phosphate is monetite calcium phosphate.

It is advantageous to conduct the reaction at a temperature higher than ambient temperature (most often between 15° C. and 25° C.), preferably higher than approximately 50° C. and still more preferentially between 60° C. and 100° C. The ideal temperature is around 90° C.

At temperatures lower than 50° C., we have observed that the reaction requires more time.

The hydrolysis reaction may be conducted by means of any concentration of aqueous brushite suspension.

The brushite is kept in suspension during hydrolysis to guarantee obtaining homogenous granules.

The reagents are preferably reacted with sufficient stirring to keep the brushite in aqueous suspension.

In practice, it is difficult to keep the brushite in suspension when the concentration is higher than approximately 50% by weight. It is advantageously between 30 and 40% by weight.

More vigorous stirring does not improve the reaction speed and may lead to a breaking up of the particles with a corresponding loss of useful yield.

The quantity of base used is close to that defined by the stoichiometry of Equation [1]. Thus, the base can be used in a quantity such that it represents 80 to 110% of the stoichiometric quantity expressed with respect to brushite calcium phosphate.

It is possible to add all of the base at the beginning of the reaction, but in the preferred process of the invention, the basic solution is added optimally in a progressive manner, i.e., in proportion to the progression of the reaction, while keeping the pH value in the predefined zone.

The basic solution can be added by any convenient method whatsoever, either directly into the aqueous suspension or by diverting a fraction of the medium by forming a circulation loop and introducing the base at the level of the diversion loop.

The pH is measured by any suitable method, either by placing a pH detector directly in the aqueous suspension, or by placing the pH detector in the previously mentioned diversion line.

Once the pH has remained stable for an appropriate period of time, approximately 30 minutes, the transformation of the brushite calcium phosphate into hydroxyapatite calcium phosphate is complete and the solid can be separated from the aqueous solution.

This can be accomplished preferably by filtration or centrifugation. The solid is washed with water and is then dried.

Washing is done with water used in a proportion such that it generally represents twice the volume of the cake.

Drying is most via air drying, preferably by heating hydroxyapatite calcium phosphate to a temperature of between 80 and 120° C. and preferably approximately 110° C. to eliminate the moisture that is physically absorbed.

The hydroxyapatite calcium phosphate that is prepared using the process of the invention is very pure, as is observed in the case of measurement by x-ray diffraction.

The granules of hydroxyapatite obtained according to the present invention can be used in the pharmaceutical field.

The applications for the granules of the invention are those for calcium phosphate.

Furthermore, they have the advantage of providing a calcium and phosphorus supplement in food.

Said elements play an important role in the makeup and functioning of nerves, bones, muscles and teeth.

More particularly, the granules of the invention have the advantage of being directly usable to formulate active ingredients by direct compression.

"Active ingredient" means any product intended for administration by oral route having a beneficial or desired effect on the user.

Thus, the active ingredient can be any product having pharmacological properties, i.e., having a preventative or curative action on a living organism.

Para-pharmaceutical products are also included, such as, for example, vitamins or trace mineral supplements that can be presented in tablet form.

As examples of therapeutic active ingredients, we can cite in a non-limiting manner anti-rheumatism drugs and nonsteroidal anti-inflammatories (ketoprofen, ibuprofen, flurbiprofen, indomethacin, phenylbutazone, allopurinol, nabumetone, etc.), opiate or non-opiate analgesics (paracetamol, phenacetin, aspirin, etc.), antitussives (codeine, codethyline, alimemazine, etc.), psychotropic drugs (trimipramine, amineptine, chlorpromazine and phenothiazine derivatives, diazepam, lorazepam, nitrazepam, meprobamate, zopiclone, and derivatives of the cyclopyrrolone family, etc.), steroids (hydrocortisone, cortisone, progesterone, testosterone, prednisolone, triamcinolone, dexamethazone, betamethazone, paramethazone, fluocinolone, beclomethazone, etc.), barbiturates (barbital, allobarbital, phenobarbital, pentobarbital, amobarbital, etc.), antimicrobial agents (pefloxacine, sparfloxacin, and derivatives of the quinolone class, tetracyclines, synergistines, metronidazole, etc.), drugs intended for the treatment of allergies, particularly anti-asthmatics, antispasmodics and antisecretory drugs (omeprazole), cerebral vasodilators (quinacainol, oxprenolol, propranolol, nicergoline, etc.), cerebral protectors, hepatic protectors, therapeutic agents for gastrointestinal disorders, contraceptives, oral vaccines, antihypertensives and cardiovascular or cardioprotective drugs such as beta-blockers and nitrated derivatives.

The quantity of activity ingredient(s) included in tablets prepared according to the process of the present invention can vary within broad limits. It is more particularly between 0.001 and 95% by weight of the total composition, the complement being assured by the matrix.

Therefore, the hydroxyapatite calcium phosphate granules of the invention are principal constituents of the matrix.

Hydroxyapatite calcium phosphate generally forms between 10% and 100% by weight of the matrix. Advantageously, it represents at least 80% and preferably at least 90% by weight of the matrix.

Advantageously, a lubricant such as magnesium stearate is added to the granules in a quantity that is generally of the order of 0.5% by weight.

A disintegrating agent can also be added to the granules to promote the final breakdown of the tablets. This agent can be a starch, notably corn starch or croscarmellose sodium incorporated in a quantity that can vary between 5 and 10% by weight.

The matrix can also have one or more pharmaceutically acceptable excipients, more particularly diluting agents, cohesion agents, lubricants and coloring agents and flavorings such as saccharides, notably lactose and saccharose, fatty acids such as stearic acid, for example; polyethylene glycol; other phosphates such as dicalcium phosphate, silica, silicoaluminates, cellulose derivatives, notably HMPC, xanthan gum, gelatin, polyvinylpyrrolidone.

The granules of the invention are mixed with the active ingredient or ingredients and possibly with the other excipients of the composition according to any known method for solid/solid mixing compressed dry by direct compression, i.e., without the use of water or an organic solvent such as ethanol.

According to the invention, the compression operation consecutive to mixing the excipients and the active ingredient(s) is generally done at a force that can range form 6 to 30 kN (measurement taken at the level of the compression roller) and preferably of the order of 10 to 20 kN. This compression operation is preferably preceded by precompression at a force that can range from 0.5 to 2.5 kN.

High compression speeds can be reached by means of the process according to the invention without altering the quality of the tablets. It is notably possible to reach speeds greater than 150,000 tablets/hour, without leading to breakage.

Tablets obtained according to the invention have the advantage of being able to release the active ingredient quickly, but also have good mechanical properties, particularly friability.

The tablets obtained have a friability measured according to the method referenced by the American Pharmacopoeia USP 26 under the No. 1216 of less than 1%.

The disintegration time measured according to the method referenced by the American Pharmacopoeia USP 26 under the No. 2040 is less than 1 minute.

In a manner more completely illustrating the nature of the invention and the method for applying it practically, Examples 1 to 4 of embodiment of the invention are given. Example 5 is comparative example where hydroxyapatite calcium phosphate is prepared by direct precipitation following precompaction into granulates.

Before giving the examples in detail, we specify the methods used to determine the different characteristics of the products obtained.

compressed and uncompressed apparent density:
Apparent density is measured in an apparatus illustrated by FIG. 6.

To begin, the empty test tube (2) is weighed.

The powder to be measured is introduced into test tube (2) by means of funnel (1) so that the top of the powder bed is even with the height of the test tube calibrated at 250 cm$^3$ (level A).

The weight of the powder is determined by weighing the full test tube.

The test tube is fastened onto support (3) by means of clamps (4).

The counter (8) that adds up the number of strikes on the bottom of the test tube is zeroed.

The test tube is subjected to vertical shocks applied at its base by means of a hammer (5) activated by a motor (6) via a cam (7). The operation is stopped when the volume obtained is constant (level B).

The changes in the apparent volume read on the test tube gradations as a function of the number of strikes applied by means of the hammer are recorded.

An experimental compression curve is obtained.

Apparent volume=f (number of strikes) that is transformed into a curve apparent density curve=f (number of strikes).

The apparent density is determined according to the equation:

$$\text{apparent density} = \frac{\text{mass of the powder introduced (g)}}{\text{apparent volume (cm}^3\text{)}}$$

Particle-Size Measurement:
Particle size is measured by laser light diffraction in aqueous suspensions without ultrasound and without dispersing agent, by means of a Beckman Coulter® LS230 particle-size analyzer, by using Mie's theory.

Bet Specific Surface:
The surface in all the examples is measured according to NF ISO standard 9277, by nitrogen adsorption using the BET method at one point and a Micromeritics Flowsorb™ surface analysis device. Before the measurement, all the samples are subjected to air drying in an oven for 2 hours at a temperature of 200° C.

Flow Capacity:
The flow capacity in all the examples is measured according to a test carried out by means of a Van-Kel™ Flowmeter model (VK10210) device.

The principle of the test consists in allowing 200 grams of material to flow through a "B" "7/16" tablet gauge. The time necessary for the 200 g of material to flow through is defined. The flowability is expressed in terms of flow rate, i.e. g/s.

Hardness of the Tablets:

The tablets are tested for hardness by using a Schleuniger Tablet Hardness Tester™, model 28/106.

The principle consists in placing the tablet between the compression jaws and exerting an increasing force until the tablet is crushed.

The force is recorded and expresses the hardness of the tablet.

The hardness indicated is the average hardness of 10 tablets.

EXAMPLES

Example 1

A brushite dicalcium phosphate having a particle size such that 90 percent of the particles are smaller than 260 microns and 90 percent of them are larger than 10 microns (DITAB product, manufactured by the Rhodia Company) is loaded at ambient temperature into a double-wall reactor in which water circulates, in a quantity such that an aqueous suspension having a concentration of 40% by weight is obtained.

The suspension is stirred by means of a mechanical stirrer and it is heated to 60° C. by means of hot water circulation.

The pH of the reaction is regulated at 8.0 by means of a pH regulator.

As soon as the pH is lower than this value, the pH is raised again by adding a 20% aqueous solution of ammonium hydroxide, expressed by a weight of $NH_3$.

Heating is maintained at a temperature of 60° C.

After 4 hours, the suspension is cooled again and the resulting solid is separated from the solution by filtration.

The solid is washed with water and is then dried at a temperature of 110° C.

The product obtained has a particle-size distribution of 90 percent smaller than 260 microns and 90 percent larger than 10 microns.

Other characteristics of the product are compiled in Table (I) below.

Example 2

The same treatment is carried out as described in Example 1, with the exception of keeping the temperature at 90° C.

Example 3

The same treatment is carried out, as described in Example 2, with the exception that the base used is a 20% aqueous sodium hydroxide solution.

Example 4

The same treatment is carried out as described in Example 3, with the exception that the base used is a 30% aqueous solution of potassium hydroxide.

Comparative Example 5

A hydroxyapatite calcium phosphate is prepared according to a standard process that consists of loading a reactor with a 12% calcium hydroxide suspension (weight/weight), loading the suspension at a temperature of 60° C. and then adding a solution of 20% $H_3PO_4$ to the lime suspension, until the pH of the resulting suspension is between 6 and 7.

The suspension is filtered on a vacuum filter and it is dried at a temperature of 110° C. in an oven for 8 hours.

Granulates are prepared by loading the dry product thus obtained into a Fitzpatrick Chilsonator® roller/compactor system, equipped with 10-cm wide and 75-cm diameter rollers.

The rollers have a surface covered with sinusoidal channels and are separated by a roller spacing of 0.05 cm.

The powdered mixture is fed by means of a moving belt into the Chilsonator® compacting device and is subjected to compacting by passage between the rollers.

One roller was driven against the other hydraulically with a pressure of 70 kg/square centimeter (manometric pressure).

The roll force is approximately 2,143 kg per linear centimeter. The rollers have a rotation speed of 16 rpm.

The product exists in the form of a sheet that is broken up by means of a Fitzmill® (model DAS06) crushing device equipped with rotating cutting blades.

The product is unloaded from the crushing device through a sieve which had round openings of 0.125 cm.

The compacted and crushed product was then directly fed into a vibrating sieving machine.

The sieves used have a diameter of 120 cm.

The first sieve was classed at 36 TBC, "tensile bolting cloth" (or a mesh opening of 541 μm), and the second sieve below was classed at 78 TBC (or a mesh opening of 231 μm).

Thus by means of these vibrating sieves the load is separated into three portions.

The median fraction of particles is recovered, i.e., all the particles that pass through the 36 TBC sieve but cannot pass through the 78 TBC sieve.

The larger and smaller fractions that emerge from the vibrating sieves are sent to the Chilsonator®, mixed with the gross feed load for the Chilsonator®, and are then recycled.

Characteristics of the Granules

FIGS. 1 to 3 given in the attachment illustrate the morphology of the hydroxyapatite calcium phosphate granules according to Example 2 of the invention (FIG. 1), of the raw material, i.e. the brushite calcium phosphate (FIG. 2) and of a hydroxyapatite calcium phosphate prepared according to the prior art described in Example 5 (FIG. 3).

Figure 1:
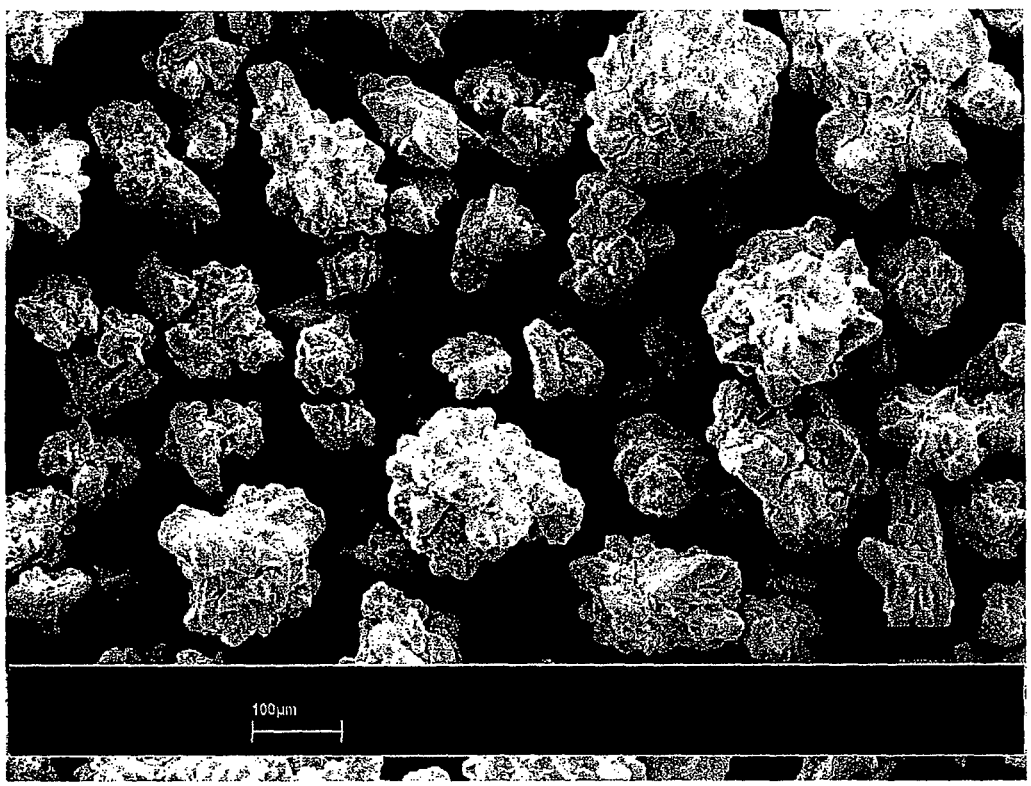
Figure 2:
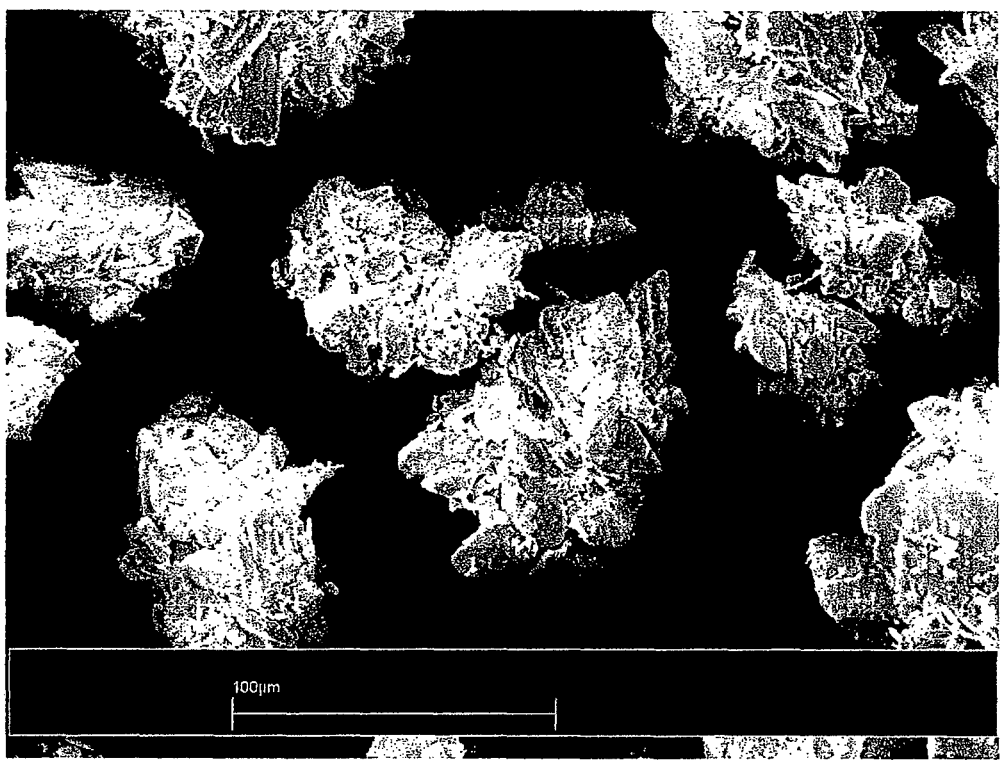
Figure 3:
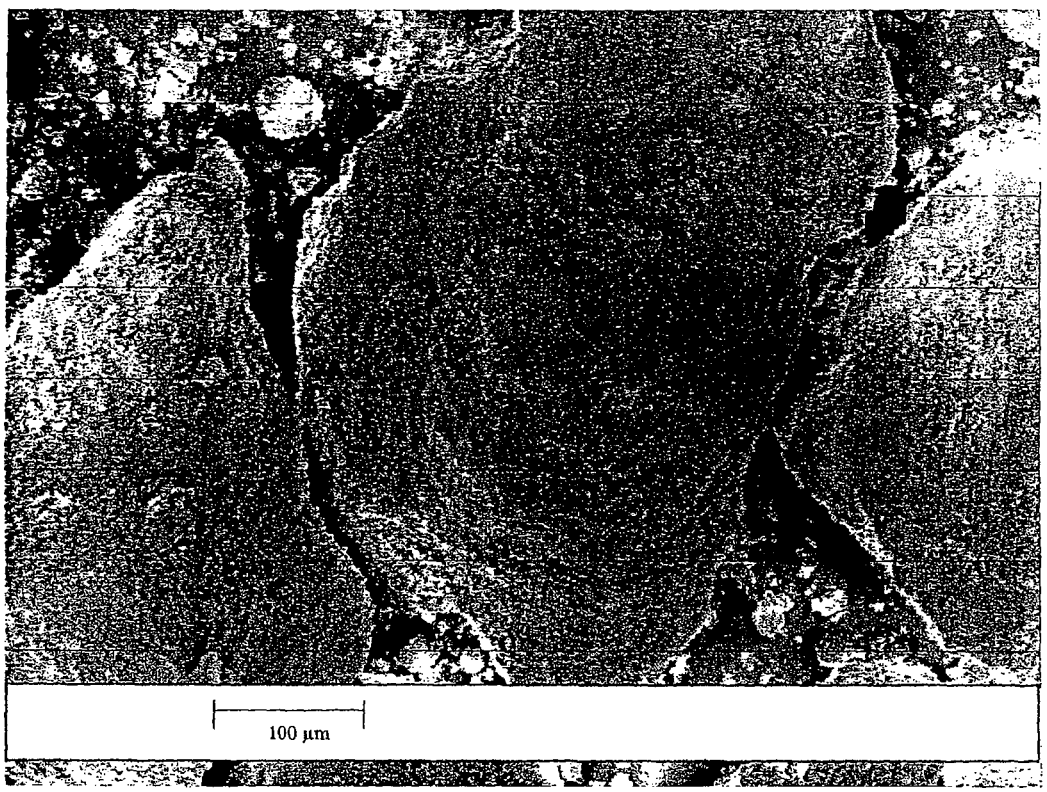
Figure 4:
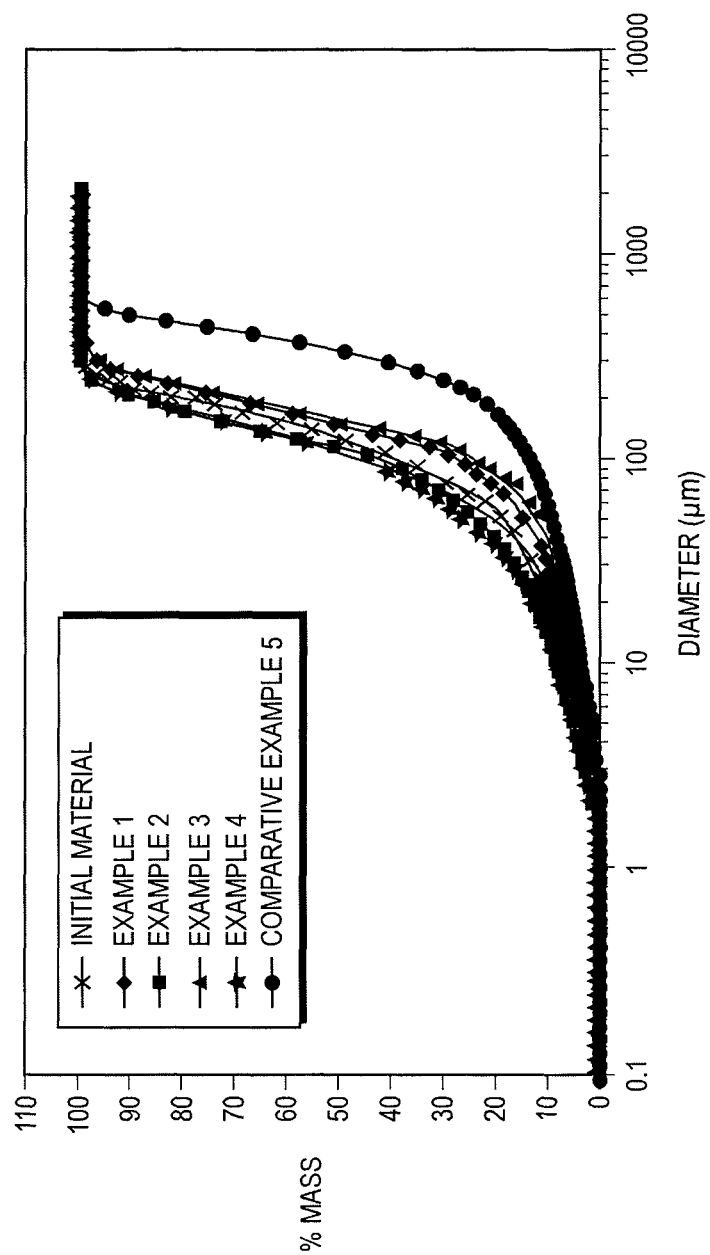
FIG. 4 shows a graph that corresponds to the cumulative curves for the determination of the median diameter ($d_{50}$) of the different examples.
Figure 5:
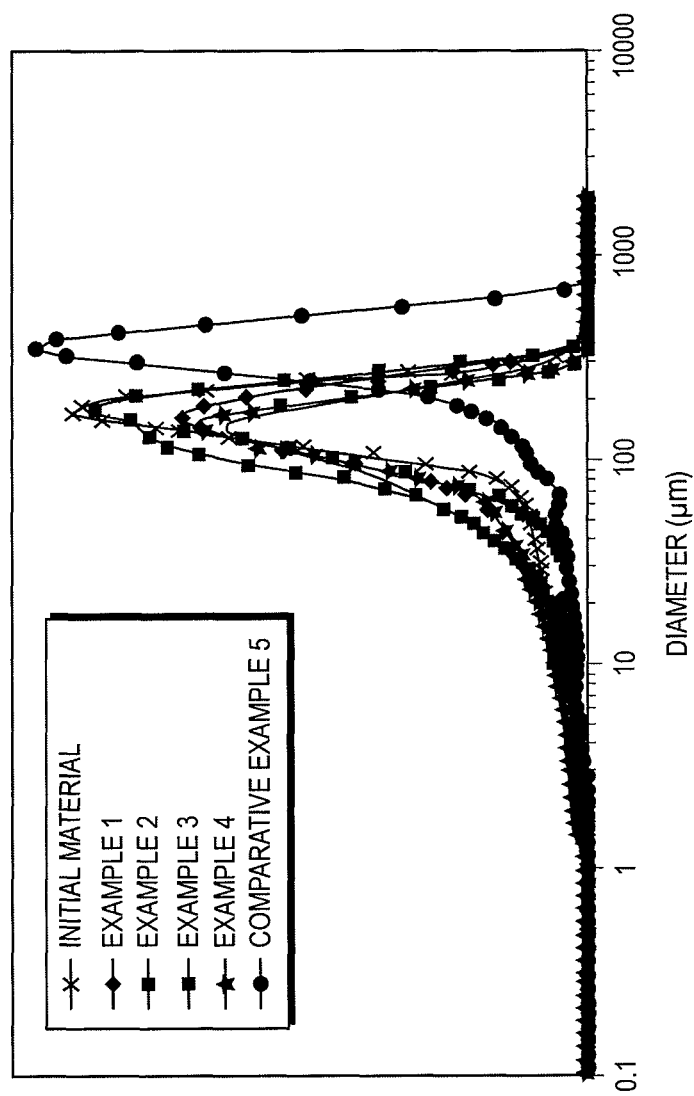
FIG. 5 represents a graph that illustrates the particle-size distribution of the different examples.
Figure 6:
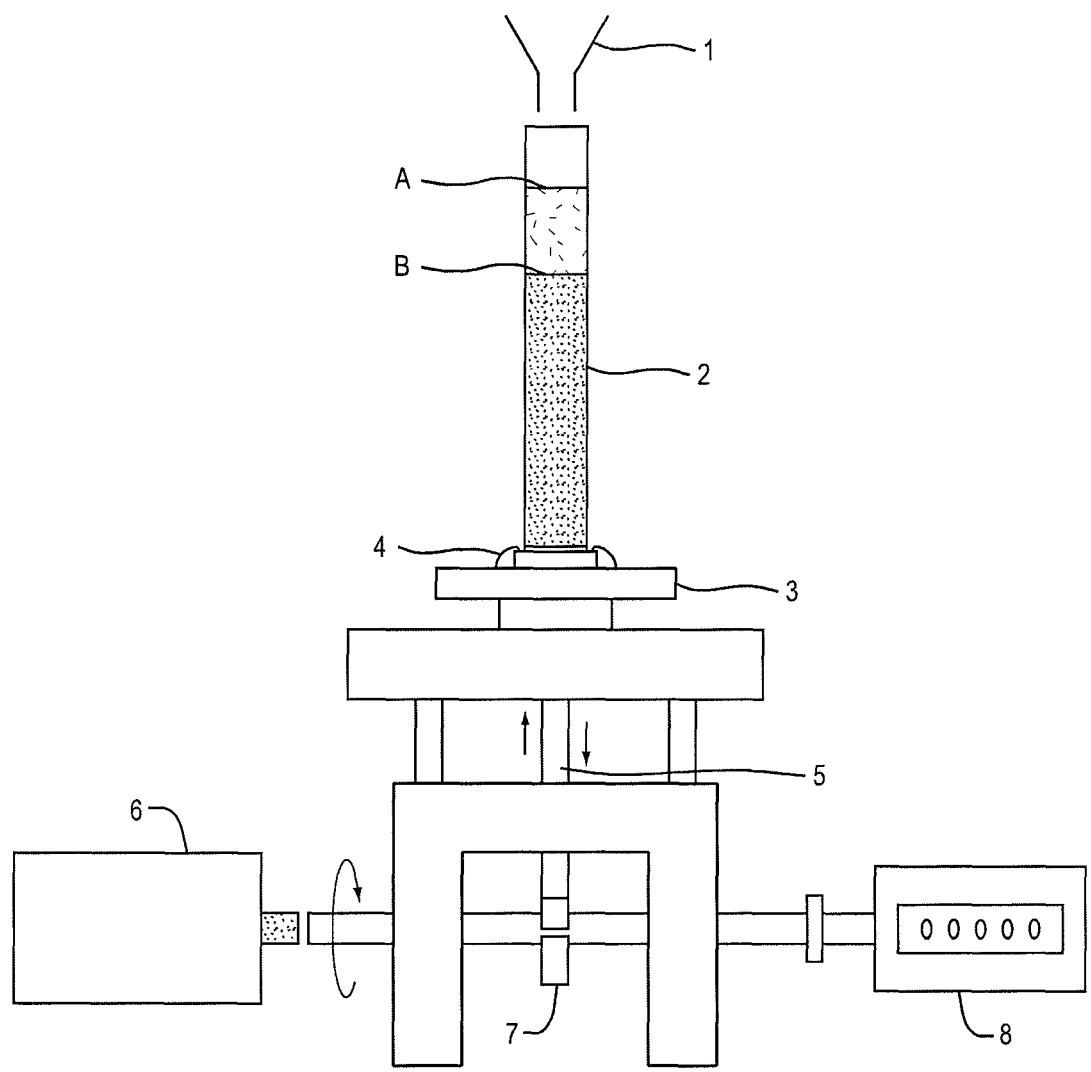

The other physicochemical characteristics of the products originating from the examples are described in Table (I).

TABLE (I)

| Material | Apparent density g/cm$^3$ | Flow capacity g/s | Specific surface m$^2$/g |
|---|---|---|---|
| Initial material | 0.870 | 33 | 2 |
| Example 1 | 0.675 | 10.4 | 60 |
| Example 2 | 0.721 | 11.9 | 53 |

TABLE (I)-continued

| Material | Apparent density g/cm³ | Flow capacity g/s | Specific surface m²/g |
|---|---|---|---|
| Example 3 | 0.720 | 11.1 | 20 |
| Example 4 | 0.932 | 13.3 | 78 |
| Comparative Example 5 | 0.872 | 16.7 | 70 |

Characteristics of the Tablets

Tablets from the examples above are prepared by placing the hydroxyapatite calcium phosphate (at a rate of 97 percent), 2% Ac-Di-Sol™ (croscarmellose stearate) disintegration agent and 0.5% magnesium stearate lubricant in a V mixer with double shell (Patterson Kelley™), equipped with an intensification bar.

The mixture is subjected to the mixing procedure for 2 minutes with the intensification bar stopped.

The formulations are compressed by direct compression on a rotating tableting machine (Manesty™ B3B), equipped with a standard IPT ⁷⁄₁₆-inch cutting tool.

The tableting machine was equipped with tensiometers attached to a recorder in order to record the compressive force applied during each lot of tablets.

4 of the 16 molds of the tableting machine are used.

The tablets are produced at a rate of 750 tablets per minute on the basis of 16 molds.

The nominal weight of the tablets is 675 mg.

The hardness characteristics of the tablets obtained after compression on the above-mentioned machine for the initial material, i.e., brushite calcium phosphate, granules of the invention obtained according to Examples 1 to 4, as well as comparative hydroxyapatite calcium phosphate from Example 5 are compiled in Table (II), which follows.

TABLE (II)

| Compressive force (kN) | Hardness of the Initial material (kPa) | Hardness of Example 1 (kPa) | Hardness of Example 2 (kPa) | Hardness of Example 3 (kPa) | Hardness of Example 4 (kPa) | Hardness of Comparative Example 5 (kPa) |
|---|---|---|---|---|---|---|
| 10 | 3 | 6.3 | 3.8 | 8.5 | 4.1 | 1.8 |
| 20 | 7.7 | 17.8 | 16.5 | 21.7 | 14.4 | 4.2 |
| 30 | 15.2 | 31.5 | 19.8 | 39.6 | 23.6 | — |

Throughout the foregoing, it can be observed that the product prepared according to the present invention (Examples 1-4) has compressibility properties that are significantly greater than those of the material prepared by a traditional method (Example 5) and has compressibility properties greater than those of the initial material [Table (II)].

The flow properties of the products prepared according to the present invention are also good, as is shown in Table (I).

Moreover, all the tablets prepared according to the present invention (Examples 1-4) have good disintegration profiles, with a dissolution rate of less than one minute.

We claim:

1. A process for preparation of calcium phosphate granules having an x-ray diffraction pattern characteristic of stoichiometric hydroxyapatite comprising (a) treating a brushite dicalcium phosphate suspension having a particle size such that 90% of the particles are smaller than 300 microns and 90% of them are larger than 10 microns with a basic solution, and (b) maintaining the pH of the suspension at least at 7.0, for a period of time sufficient to permit the transformation of brushite calcium phosphate into stoichiometric hydroxyapatite calcium phosphate having a particle size such that 90% of the particles are smaller than 300 microns and 90% of them than 10 microns.

2. The process according to claim 1, wherein the size of the particles of brushite dicalcium phosphate is such that the median diameter ($d_{50}$) is between 100 .mu.m and 250 .mu.m.

3. The process according to claim 1, wherein the base used in the basic solution is selected from the group consisting of: NaOH, KOH, and NH$_4$OH.

4. The process according to claim 1, wherein the pH of the brushite dicalcium phosphate suspension is maintained between 7.0 and 10.0.

5. The process according to claim 1, wherein the temperature of the brushite dicalcium phosphate suspension is maintained at greater than 50.degree. C. during the reaction with the basic solution.

6. The process according to claim 5, wherein the temperature of the brushite dicalcium phosphate suspension is maintained at is approximately 90.degree. C. during the reaction with the basic solution.

7. The process according to claim 1, wherein a sufficient volume of the base solution is added to achieve 80 to 110% of the stoichiometric quantity expressed with respect to the brushite dicalcium phosphate.

8. The process according to claim 1, wherein the brushite dicalcium phosphate suspension is first heated to the chosen reaction temperature then he base solution is introduced while regulating the pH.

9. The process according to claim 1, wherein first the base solution is added so as to regulate the pH and then the medium is heated to the chosen reaction temperature.

10. The process according to claim 1, wherein the basic solution is added progressively while monitoring the pH to maintain the pH of the suspension within a predefined range.

11. The process according to claim 1, further comprising the step of separating the stoichiometric hydroxyapatite calcium phosphate from the aqueous solution by one of filtration or centrifugation.

12. The process according to claim 1, further comprising the step of drying the stoichiometric hydroxyapatite calcium phosphate at a temperature between 80 and 120.degree. C.

* * * * *